(12) United States Patent
Lechmann et al.

(10) Patent No.: US 7,704,280 B2
(45) Date of Patent: Apr. 27, 2010

(54) INTERVERTEBRAL IMPLANT COMPRISING TEMPORARY BLOCKING MEANS

(75) Inventors: Beat Lechmann, Bettlach (CH); Roger Bürki, Balsthal (CH); Robert Frigg, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 1117 days.

(21) Appl. No.: 11/338,453

(22) Filed: Jan. 23, 2006

(65) Prior Publication Data
US 2006/0229724 A1 Oct. 12, 2006

Related U.S. Application Data

(63) Continuation of application No. PCT/CH03/00496, filed on Jul. 22, 2003.

(51) Int. Cl.
*A61F 2/44* (2006.01)
(52) U.S. Cl. ............ 623/17.15; 623/17.11; 623/17.16; 606/246
(58) Field of Classification Search ......... 606/246–249; 623/17.11–17.16, 86 A
See application file for complete search history.

(56) References Cited

U.S. PATENT DOCUMENTS

| | | | |
|---|---|---|---|
| 5,314,477 A | 5/1994 | Marnay | |
| 5,556,431 A | 9/1996 | Büttner-Janz | |
| 6,517,580 B1 * | 2/2003 | Ramadan et al. | ......... 623/17.15 |
| 7,473,276 B2 | 1/2009 | Aebi et al. | |
| 2003/0176923 A1 * | 9/2003 | Keller et al. | ............. 623/17.14 |
| 2004/0117022 A1 * | 6/2004 | Marnay et al. | ........... 623/17.16 |
| 2004/0143332 A1 | 7/2004 | Krueger et al. | |
| 2006/0122703 A1 | 6/2006 | Aebi | |

FOREIGN PATENT DOCUMENTS

| | | |
|---|---|---|
| FR | 2 737 656 | 2/1997 |
| WO | WO 2004/054475 | 7/2004 |
| WO | WO 2004/054478 A1 | 7/2004 |

OTHER PUBLICATIONS

"First Notice of Reason for Rejection" issued by the Japanese Patent Office.

(Continued)

*Primary Examiner*—Eduardo C Robert
*Assistant Examiner*—Christina Negrelli
(74) *Attorney, Agent, or Firm*—Stroock & Stroock & Lavan LLP (57) ABSTRACT

An intervertebral implant including a top part, a bottom part and a joint arranged axially between the top part and the bottom part. The top part includes a top surface suitable to be placed on the base plate of a body of the vertebra adjacent and above the site of removal. The bottom part has a bottom surface suitable to be placed on the cover plate of a body of the vertebra adjacent and below the site of removal. The joint includes a convex joint part with a first articular surface and a joint shell matching it, with a second articular surface mounted in a sliding manner on the first articular surface. The intervertebral implant including a temporarily locking mechanism to fix the two parts relative to one another.

9 Claims, 10 Drawing Sheets

OTHER PUBLICATIONS

Search Report from the European Patent Office for European Patent Application No. 03 739 938.3-2310 dated Oct. 30, 2007.

International Search Report from the European Patent Office for PCT Application No. PCT/CH03/00496 dated Mar. 26, 2004 with translation.

International Preliminary Examination Report from the European Patent Office for PCT Application No. PCT/CH03/00496 dated Aug. 4, 2005.

Chinese Office Action, issued on Mar. 13, 2009 for Chinese Patent Application No. 03826781.0.

Translated International Preliminary Report dated Apr. 30, 2009.

* cited by examiner

INTERVERTEBRAL IMPLANT COMPRISING TEMPORARY BLOCKING MEANS

CROSS-REFERENCE TO RELATED APPLICATION

This application is a continuation of International Patent Publication PCT/CH2003/000496, filed Jul. 22, 2003, which is incorporated by reference herein in its entirety.

FIELD OF THE INVENTION

The present invention relates to an intervertebral implant and, more particularly, to an artificial intervertebral implant.

BACKGROUND OF THE INVENTION

Intervertebral disks often become damaged creating discomfort for a patient. It is known that partial or total removal of a damaged disk may alleviate some of this discomfort but may limit the natural function of the spine. Thus, nowadays following the removal of a damaged, natural intervertebral disk or a damaged nucleus pulposus of a natural intervertebral disk, implants or prosthesises are placed in the intervertebral space between the two vertebra adjacent to the site of removal. The aim of implanting such implants is to bring about as natural state as possible, particularly duplicating the original height of the intervertebral disk and consequently restoring the original distance between two adjacent bodies of the vertebra. Furthermore, movements of adjacent bodies of the vertebra relative to one another should be able to be carried out with minimal hindrance of their natural function. For this purpose the retention of the ability to move when bending forward or backward, i.e. the flexion and the extension of the bodies of the vertebra as well as the lateral bending of the intervertebral bodies within the natural limits, is desirable. It is also desirable that the natural ligaments and muscles along the spine are left substantially intact, to further stabilize the movements of a mechanical replacement for a interverte-bral disk.

Intervertebral implants for maintaining the displacement between vertebrae adjacent to a removed intervertebral disc and for allowing the movement of vertebra with respect to one another are known in the art. For example, U.S. Pat. No. 5,556,431 to Büttner shows an implant comprising a bottom cover plate and a top cover plate, the external surfaces of which can be placed on, respectively, adjacent vertebra as well as a joint provided between the cover plates. This joint substantially consists of a spherical convex joint part and, two matching joint shells connected with the cover plates, so that the cover plates can polyaxially pivot relative to one another.

One disadvantage of this known construction is, that although the two cover plates are each connected with a joint part, the joint parts are not held together. This requires the implant to be assembled by the surgeon creating a possibility for erroneous assembly. Further, it creates a possibility that the implant will fall apart prior to and during implantation, risking damage to surrounding tissue and risking loss of parts.

SUMMARY OF THE INVENTION

The described intervertebral implant allows pre-assembly of the parts in a state wherein they are locked relative to one another and can be unlocked in-situ. Further, advantages of the present invention are that the joint parts are connected with the cover plates, so that they cannot move and damage the surrounding tissue. And additionally by virtue of the design of the present invention lower manufacturing costs can be achieved.

The intervertebral implant herein described includes a top part and a bottom part connected by a joint. The top part has a top surface for contacting a vertebrae adjacent and above the implant. The top part also has a dorsal side surface, a ventral side surface, a first top lateral side surface and a second top lateral side surface. The bottom part has a bottom surface for contacting a vertebrae adjacent and below the implant. The bottom part also has a dorsal side surface, a ventral side surface, a first bottom lateral side surface and a second bottom lateral side surface. Further the implant has a central plane between the first top lateral side surface and the second top lateral side surface, and between the first bottom lateral side surface and the second bottom lateral side surface. The central plane substantially bisects the top part and substantially bisects the bottom part. Additionally the implant has a central axis lying in the central plane and intersecting the top part and the bottom part. The joint is arranged between the top part and the bottom part and comprises a convex joint part having an articular surface and a joint shell having an articular surface matching the joint shell and mounted in a sliding manner on joint part. The implant also contains a temporary locking means able to temporarily fix the top part and bottom part relative to one another.

In one embodiment the temporary locking means is made from one piece and may be elastically deformable.

In another embodiment the top surface of the top part comprises at least a first top groove whose longitudinal axis intersects the ventral side of the top part and the bottom surface of the bottom part comprises at least a first bottom groove whose longitudinal axis intersects the ventral side of the bottom part.

In a further embodiment the top part comprises at least a first top groove whose longitudinal axis intersects the ventral side of the top part and lies substantially below the top surface of the top part. The bottom part comprises at least a first bottom groove whose longitudinal axis intersects the ventral side of the top part and lies substantially below the top surface of the top part. The cross-section of the grooves perpendicular to the central plane may narrow towards the top and bottom surfaces, respectively, of the top part and the bottom part. In such an embodiment, the temporary locking means may comprise a joining web that comprises a first end and a second end and is arranged parallel to the central axis and wherein the joining web has at each end a transverse web.

In another embodiment the top part comprises at least a first top groove and a second top groove, respectively, whose longitudinal axis intersects the ventral side of the top part and lies substantially below the top surface of the top part. The bottom part comprises at least a first bottom groove and a second bottom groove, respectively, whose longitudinal axis intersects the ventral side of the top part and lies substantially below the top surface of the top part. And the first and second top grooves or the first and second bottom grooves are curved having an arch-shaped longitudinal axis, and wherein the distance of the longitudinal axis from the central plane decreases as away from the ventral side. In such an embodiment the temporary locking means may have a pliers-like construction and comprise two jaws which can move relative to one another about a pivot hinge and can be introduced into the grooves. Further the axis of rotation of the pivot hinge of the temporary locking means may extend parallel to the central axis.

In a further embodiment the top part comprises at least a first top groove. The first top groove has a longitudinal axis intersecting the ventral side of the top part and lies substantially below the top surface of the top part. The bottom part comprises at least a first bottom groove. The first bottom groove has a longitudinal axis intersecting the ventral side of the top part and lies substantially below the top surface of the top part. The first top groove and the first bottom groove may have a substantially T shaped cross section. The temporary locking means may be simultaneously inserted into both the first top groove and the second bottom groove. Further the temporary locking means may comprise a web with a first end and a second end and a first flange and a second flange located on the first and second end respectively and substantially perpendicular to the web.

In a further embodiment at least one of the articular surfaces are coated with a material with a low coefficient of friction. Exemplary materials may include titanium carbide and amorphous carbon.

In another embodiment the top part and bottom part are coated with titanium on the apposed surfaces.

In a further embodiment the top surface of the top part and the bottom surface of the bottom part have a convex construction.

In another embodiment the top surface of the top part and the bottom surface of the bottom part are provided at least partially with macroscopic structures. Such macroscopic structures may comprise protuberances and the protuberances may be pyramidal. Such pyramidal protuberance may have a volume between about 0.12 $mm^3$ and about 1.4 $mm^3$. At least one protuberances may be a wedge-shaped rib such that is symmetrical about the central plane and preferably is situated in a straight line parallel to the central plane. At least one protuberance may be a saw-tooth like serration arranged symmetrically about the central plane. The protuberances may be coated at least partially with material that can be integrated into bone. Such coatings may include hydroxylapatite or a bi-phased hydroxylapatite-tricalcium phosphate mixture.

In a further embodiment the temporary locking means has a maximum volume of about 12 $cm^3$ and may be preferably about 6 $cm^3$.

In another embodiment, the implant and temporary locking means comprise a sterile packaging.

A method for inserting the device disclosed above includes inserting the intervertebral implant into a patient such that the top surface and bottom surface, respectively, are adjacent the vertebrae above and below a removed intervertebral disk and then unlocking the temporary locking means.

BRIEF DESCRIPTION OF THE DRAWINGS

The features of the invention will be better understood by reference to the accompanying drawings which illustrate presently preferred embodiments of the invention. It will nevertheless be understood that the invention should not be limited to such preferred embodiments and that the features may be used singularly or in combinations and that modification and alterations of the illustrated and described devices and methods are contemplated. In the drawings.

DETAILED DESCRIPTION OF THE INVENTION

The intervertebral implant 1 illustrated in FIGS. 1-3 substantially comprises a top part 3 with a top apposed surface 35 that intersects the central axis 2, to be placed on the base plate of the body of the adjacent vertebra located above, a bottom part 4 with a bottom apposed surface 45 that intersects the central axis 2, to be placed on the cover plate of the body of the adjacent vertebra located below, and a joint 9, provided between the two parts 3, 4, for the articulated joining of the two parts 3, 4. The joint 9 has a two-part construction comprising a convex joint part 12 and a joint shell 13. The convex joint part 12 has a spherical construction, a first articular surface 10 and is operatively associated with the bottom part 4. The joint shell 13, preferably has a second articular surface 11 matching the first articular surface 10 of the convex joint part 12, and is operatively associated with the top part 3. The top part 3 and the joint shell 13 preferably are made of two parts in the embodiment illustrated here, so that the top part 3 may be manufactured, for example, from titanium or a cobalt-chromium alloy and the joint shell 13, for example, from a plastic material although other suitable combinations of materials or a homogenous construction will be known to one of skill in the art.

Each of the top part 3 and bottom part 4 comprise a ventral side surface 31, 41, a dorsal side surface 32, 42, as well as two lateral side surfaces 33, 34, 43, 44. There is a central plane 19 between the lateral side surfaces 33, 34, 43, 44 and the central axis 2 is situated in this central plane 19 when the joint 9 is in a non-articulated state.

Macroscopic structures may be located on the top apposed surface 35 and the bottom apposed surface 45, preferably as protuberances 18. In one embodiment, the protuberances 18 are constructed as pyramid-like protuberances 17. The pyramid-shaped protuberances have preferably a volume between about 0.12 mm³ and about 1.4 mm³.

Furthermore, the top part 3 and bottom part 4 comprise means 20 to accommodate locking means 21 which can be temporarily fastened and are intended for the detachable fixing of the top part 3 and bottom part 4 relative to one another. In this case the means 20 comprise two grooves 22, 23 on the top part 3 and the bottom part 4. The longitudinal axes of the grooves 22, 23 preferably are symmetrically distanced from the central plane 19 of the intervertebral implant 1. At the same time one top groove 22a and one bottom groove 23a may be provided substantially equidistant on the left side of the central plane 19 and one top groove 22b and one bottom groove 23b may be provided substantially equidistant on the right side of the central plane 19. The grooves 22, 23 terminate in the respective ventral side surfaces 31, 41, so that the locking means 21 can be ventrally introduced into and extracted from the grooves 22, 23. Furthermore, the grooves 22, 23 preferably are open towards the apposed surfaces 35, 45.

Each of the two locking means 21 is constructed as a U-shaped clamp with two legs 27 and a web 28 joining the legs 27, in such a manner that on one side of the central plane 19 one leg 27 of one clamp can be introduced into a top groove 22a and the other leg 27 of the same clamp into the bottom groove 23a, so that the clamp is arranged parallel to the central plane 19. In a similar manner the legs 27 of a second clamp can be introduced into the grooves 22b, 23b on the other side of the central plane 19. The clamps can be elastically deformed parallel to the central axis 2, so that after their introduction into the grooves 22, 23 the legs 27 are spread and the locking means 21 can be detachably fastened to the two parts 3, 4 by an automatic elastic clamping effect. In their various embodiments the locking means 21 preferably has a maximum volume of about 12 cm³ and more preferably about 6 cm³. Providing two locking means 21 on either side of the central plane 19 provides the advantage of creating a stable fixing of the top part 3 and bottom part 4. Further where the fixing means 21 are substantially symmetrical about the central plane 19 in-situ manipulation of the surgical instruments is simplified. The locking means 21 may be made elastically deformable by using materials for the legs or web that are elastic.

Figure 1:
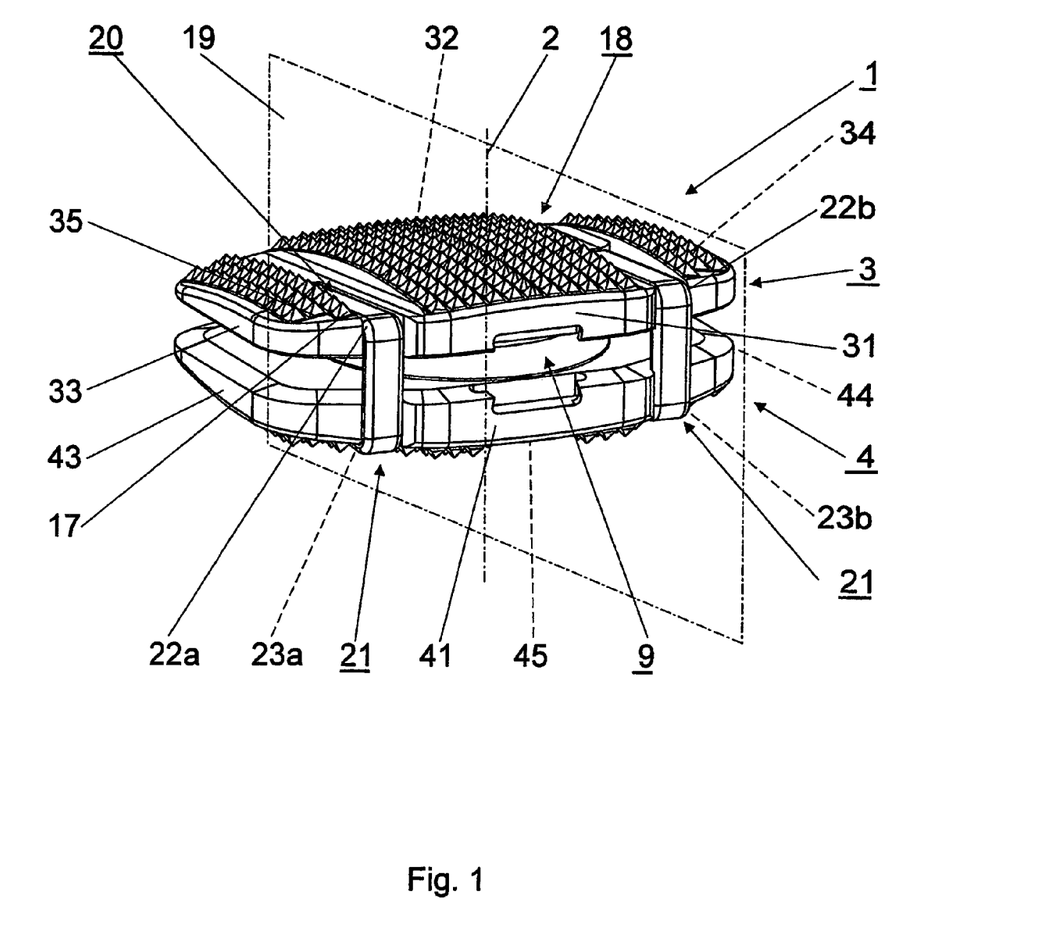
FIG. 1 is a perspective view of an embodiment of an assembled intervertebral implant with locking means.
Figure 2:
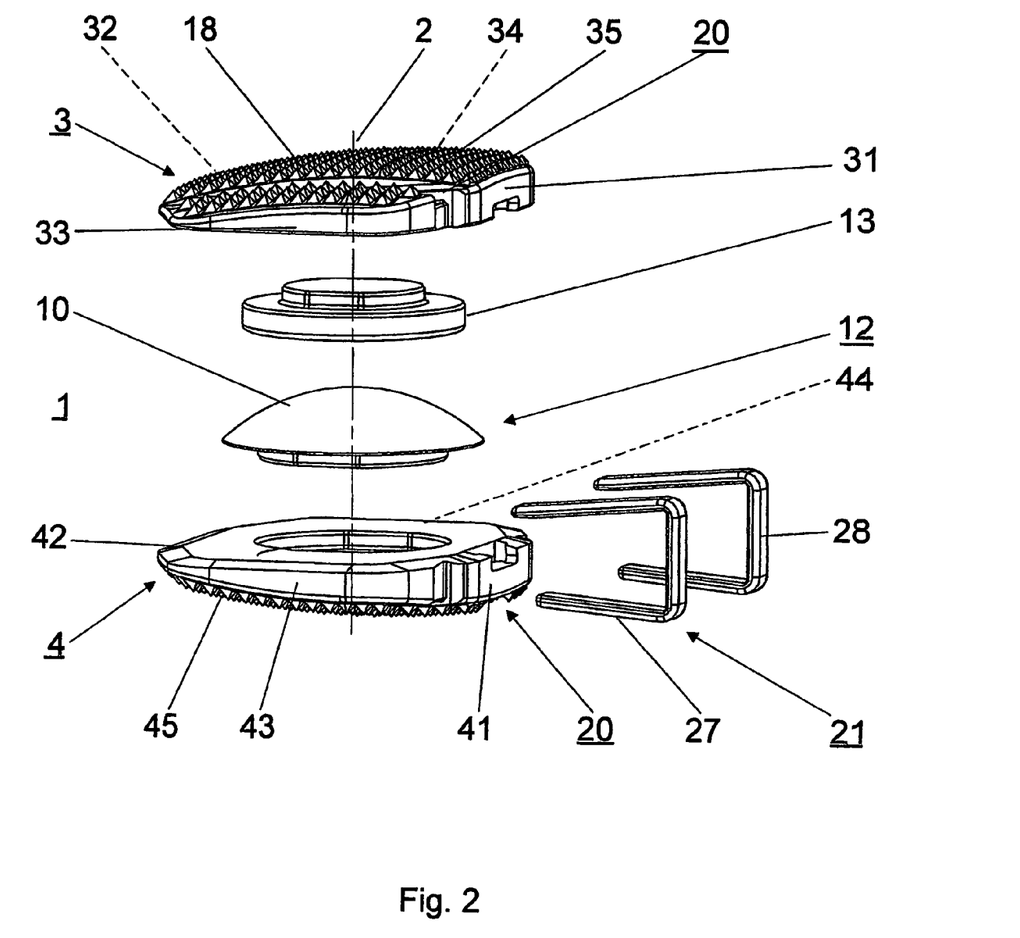
FIG. 2 is an exploded view of the embodiment of the intervertebral implant with locking means, illustrated in FIG. 1.
Figure 3:
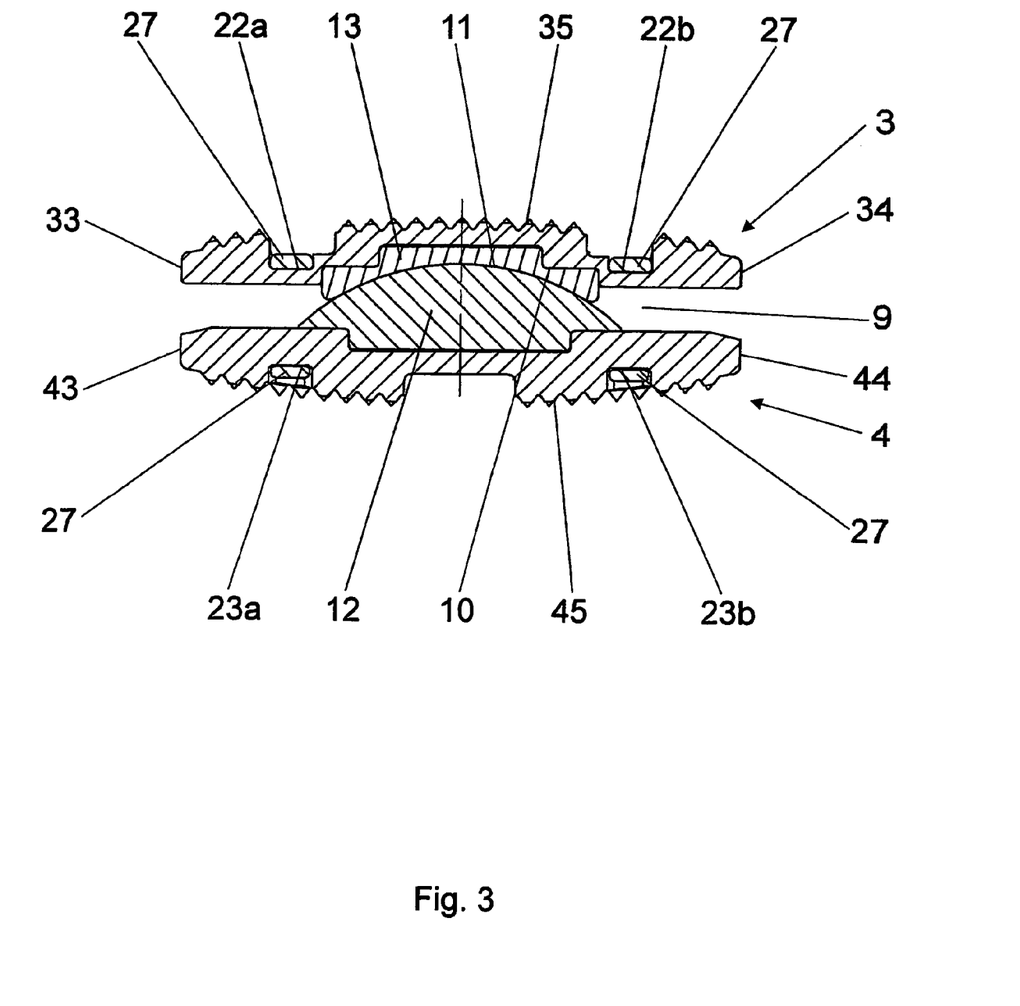
FIG. 3 is a mediolateral section of the embodiment of the intervertebral implant with locking means, illustrated in FIGS. 1 and 2.
Figure 4:
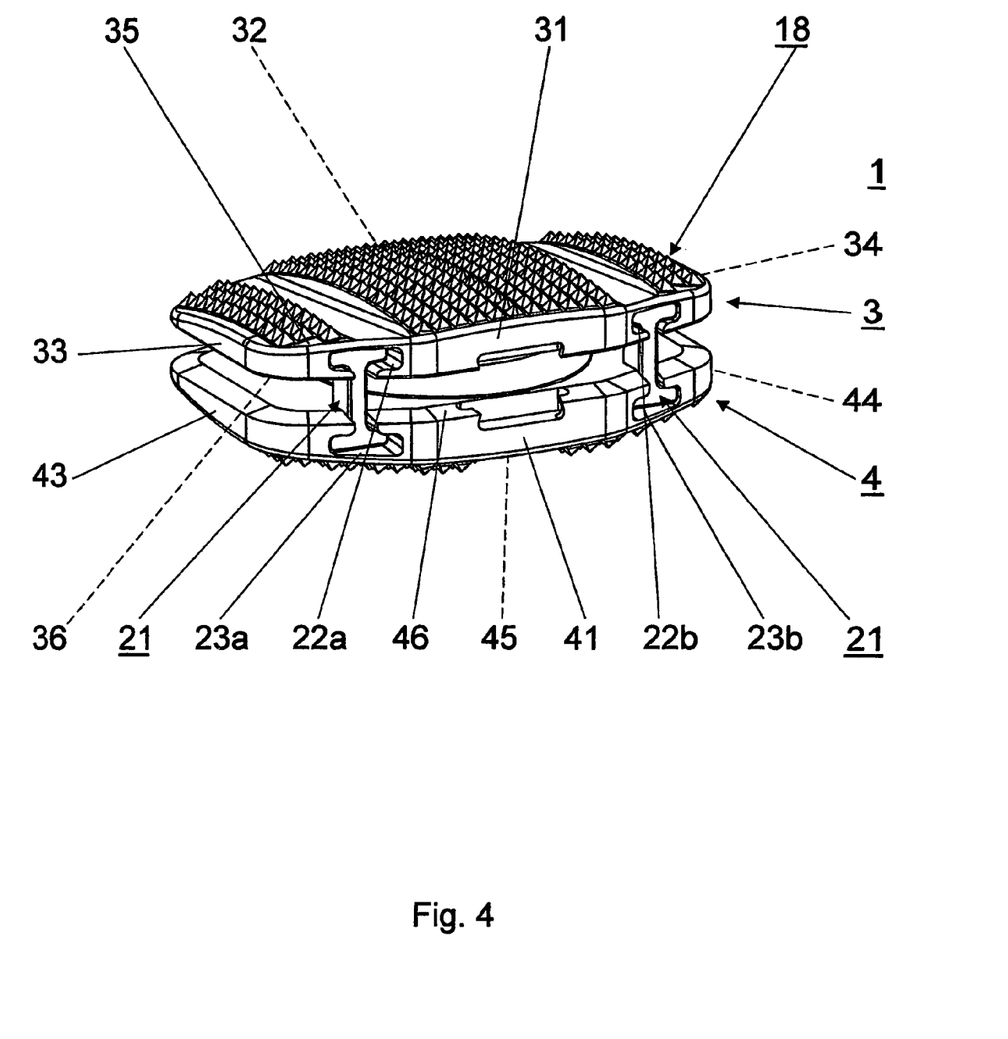
FIG. 4 is a perspective view of another embodiment of the intervertebral implant with the locking means inserted into the grooves.
Figure 5:
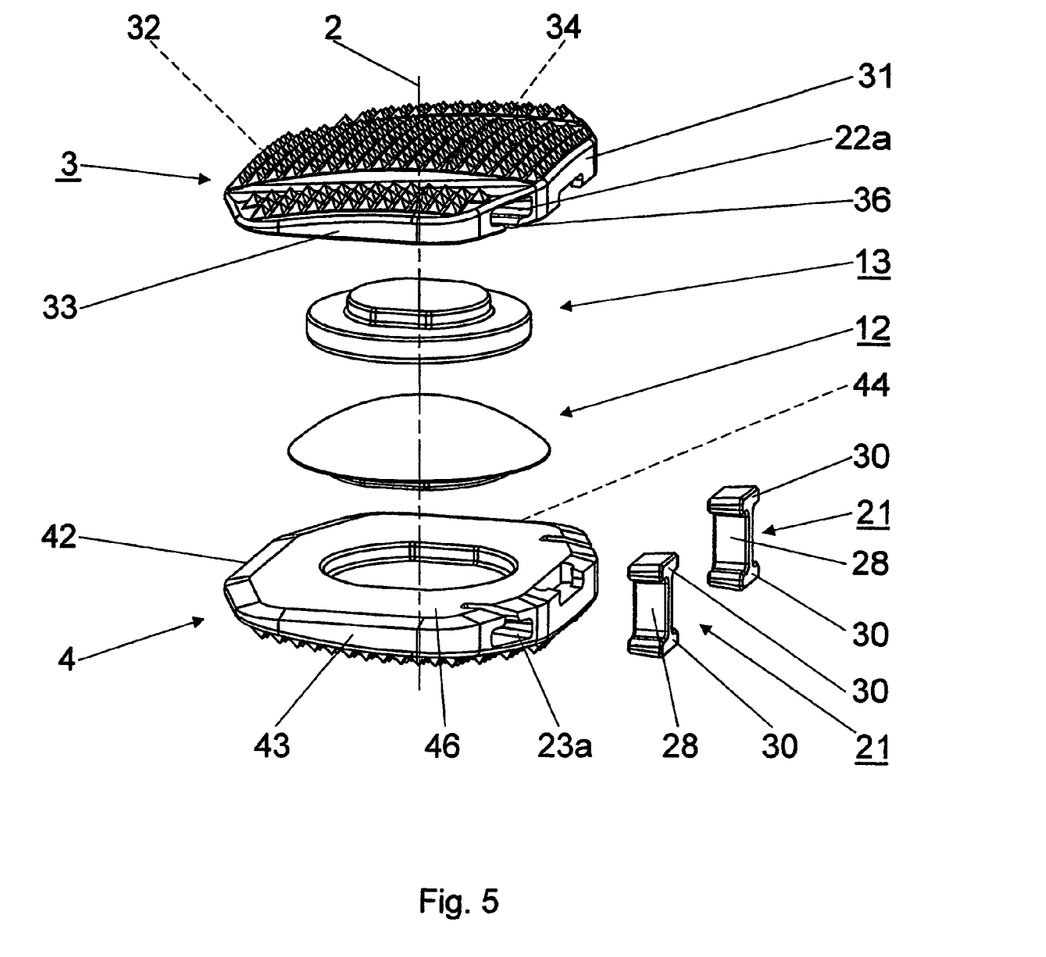
FIG. 5 is an exploded view of the embodiment of the intervertebral implant with locking means, illustrated in FIG. 4.
Figure 6:
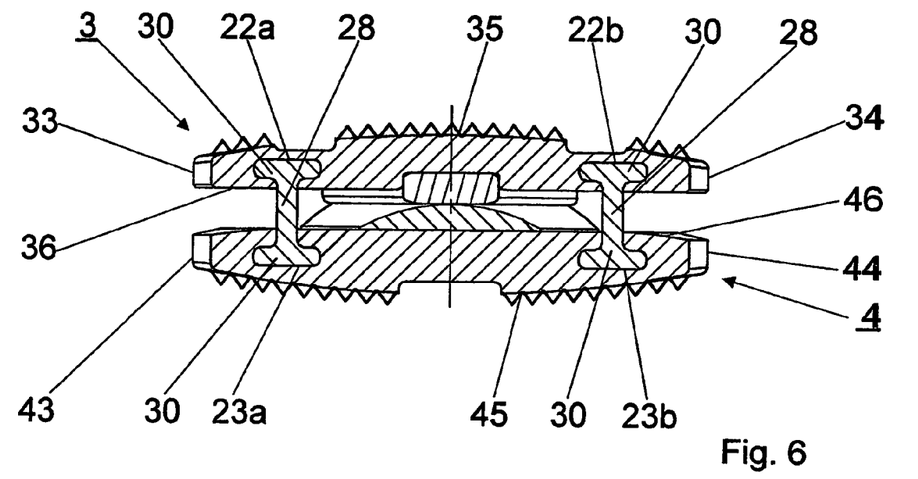
FIG. 6 is a section, parallel to the medioislateral plane, through the grooves and the locking means of the embodiment of the intervertebral implant with locking means, illustrated in FIGS. 4 and 5.
Figure 7:
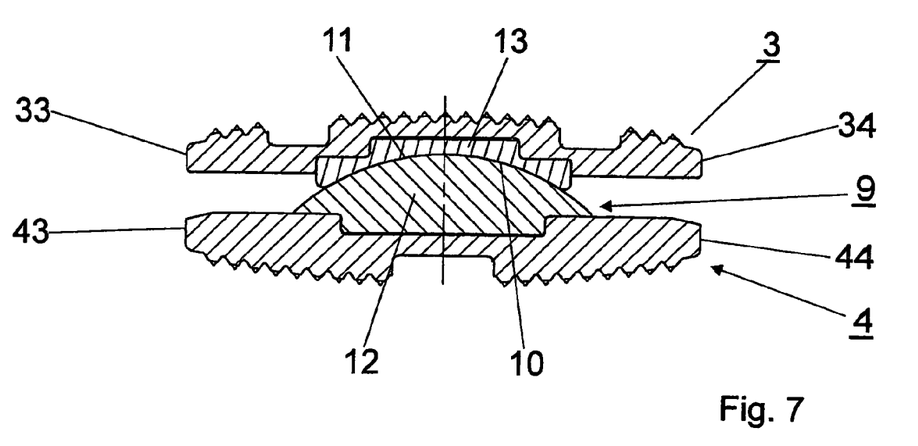
FIG. 7 is a medioislateral section through the embodiment of the intervertebral implant with locking means, illustrated in FIGS. 4 and 5.

The embodiment illustrated in FIGS. 4-7 differs from the embodiment illustrated in FIGS. 1-3 by a different construction of the grooves 22, 23 and the locking means 21. The grooves 22, 23 are open away from the top and the bottom surfaces 35, 45, respectively, of the two parts 3, 4. In addition, the grooves 22, 23 narrow away from the top and bottom surfaces 35, 45, respectively, i.e. constructed as dovetail guides. Furthermore, the two locking means 21 have a double-T type shape and comprise a joining web 28 and a transverse web 30 on each end of the joining web 28. The locking means 21 can be introduced into the grooves 22, 23 on each side of the central plane 19. The cross-section of the grooves 22, 23 decreases with the increasing distance from the ventral side surfaces 31, 41, so that when being introduced into the grooves 22, 23 the locking means 21 become wedged in them and will be detachably fasten the top part 3 and bottom part 4. Such a wedge mechanism creates an automatic fixation of the top part 3 and bottom part 4 and obviates the need for other manual fixation.

Figure 8:
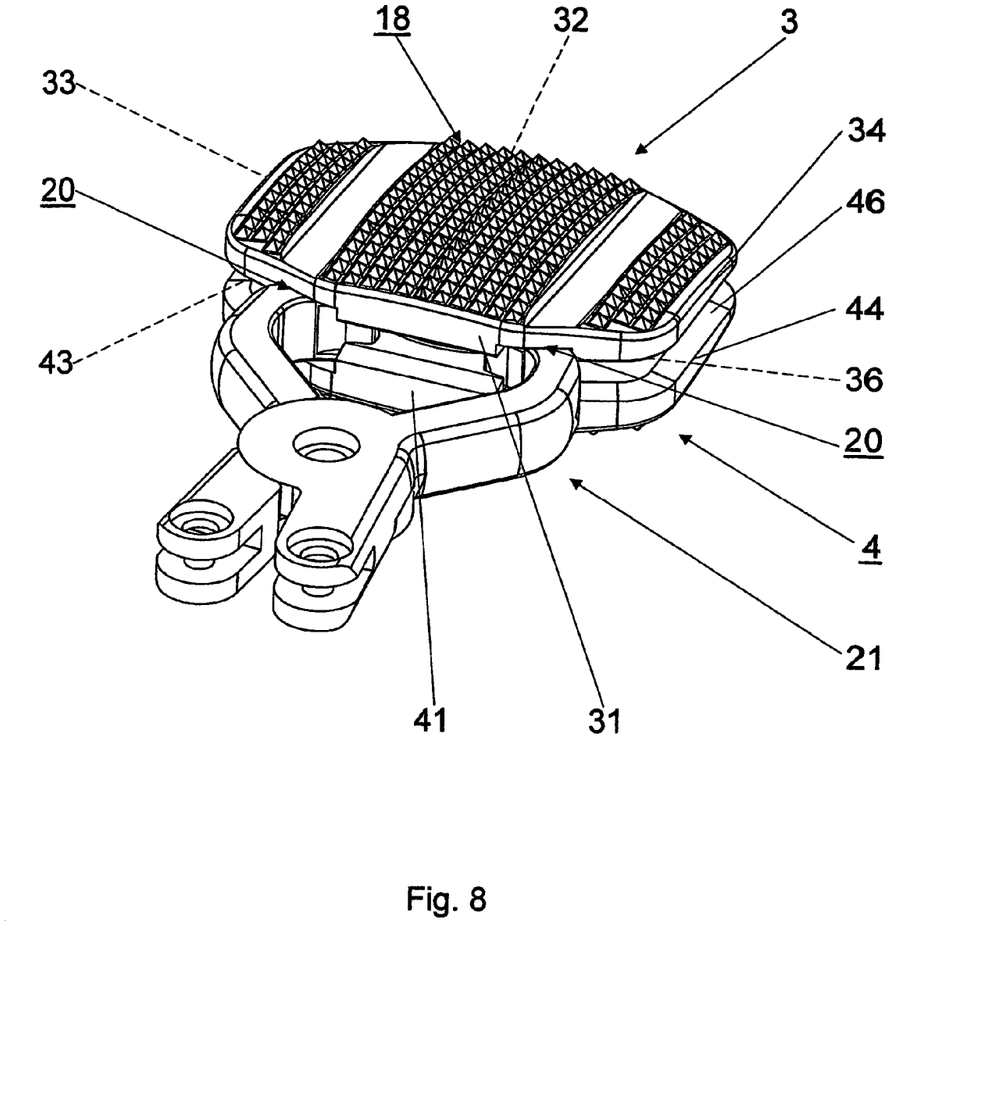
FIG. 8 is a perspective view of a further embodiment of the intervertebral implant, with the locking means inserted into the grooves.
Figure 9:
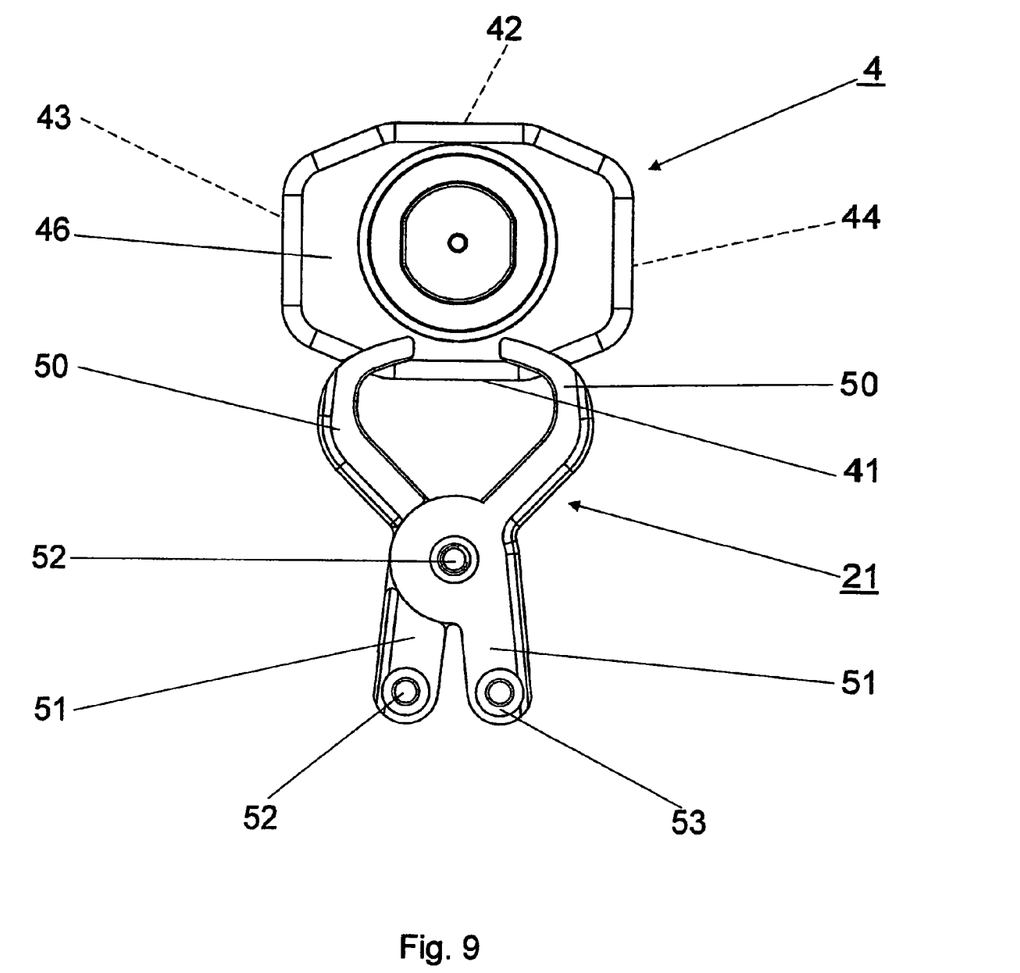
FIG. 9 is a perspective view of the bottom part of the embodiment of the intervertebral implant illustrated in FIG. 8, with the locking means retracted from the grooves.
Figure 10:
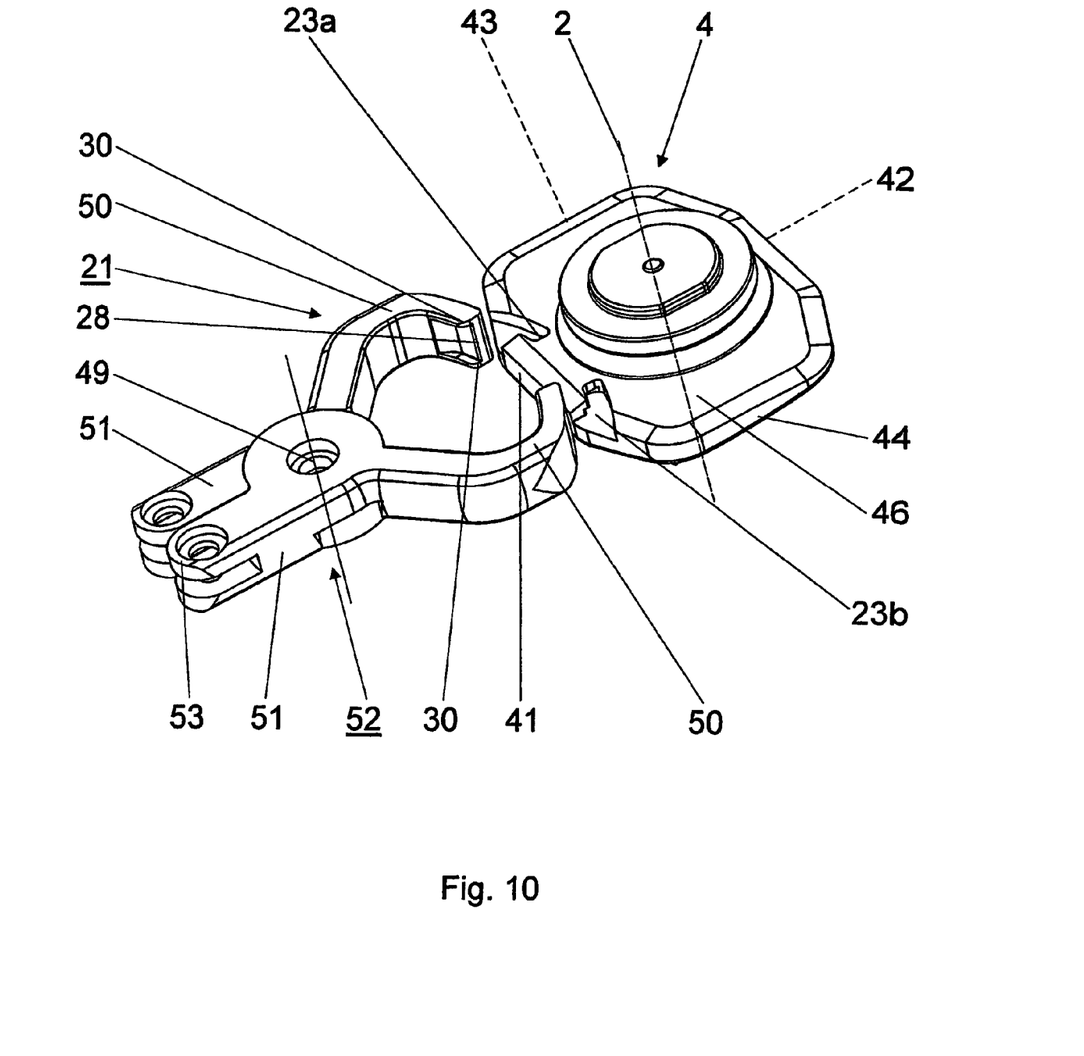
FIG. 10 is a top view of the bottom part of the embodiment of the intervertebral implant illustrated in FIGS. 8 and 9, with the locking means introduced into the grooves.

FIGS. 8-10 illustrate an embodiment, which differs from that in FIGS. 1-7 only by a different construction of the grooves 22, 23 and of the locking means 21. The grooves 22, 23 are open away from the top and bottom surface 35, 45, respectively, of the two parts and have curved longitudinal axes. The curvature of the grooves 22, 23 is so designed, that the distance between two grooves 22, 23 provided on the top part 3 or bottom part 4 decrease as the distance from the ventral side surface 31, 41 increases. Furthermore, the top groove 22 and bottom groove 23 enlarge towards the top surface 35 and the bottom surface 45 respectively. The locking means 21 have a pliers-like construction, comprising two jaws 50 which can be introduced into the curved grooves 22, 23, with levers 51, that are joined by a pivot hinge 52 in a manner that they can pivot relative to one another. The axis of rotation 49 of the pivot hinge 52 is parallel with the central axis 2. The jaws 50 have a U-shaped cross-section and comprise a joining web 28 each that is substantially parallel with the central axis 2 and two transverse webs 30 each at their ends, so that when the jaws 50 are introduced into the grooves 22, 23, the two parts 3, 4 are also fixed substantially parallel to the central axis 2. At the free ends 53 of the lever 51 an instrument can be fastened, with which the intervertebral implant 1 can be introduced into the intervertebral space and after the implantation the locking means 21 can be simply extracted from the grooves 22, 23.

Figure 11:
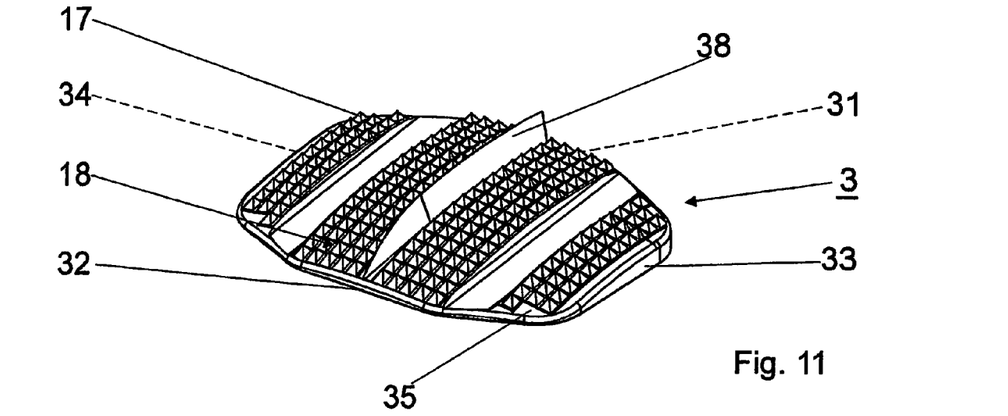
FIG. 11 is a perspective view of the top part of an embodiment of the intervertebral implant with locking means.
Figure 12:
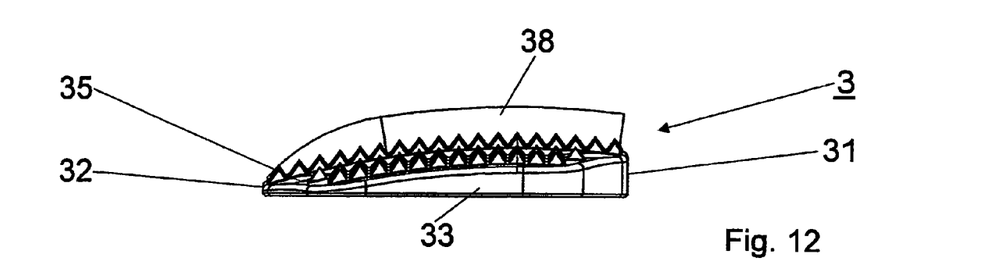
FIG. 12 is a lateral view of the top part of the embodiment of the intervertebral implant illustrated in FIG. 5 with locking means.

In addition to the pyramid-like protuberances 17 illustrated in FIGS. 1-10, the protuberances 18, as illustrated in FIGS. 11 and 12, may comprise a wedge-shaped rib 38 on the top apposed surface 35 and the bottom apposed surface 45. The rib is taller than the pyramid-like protuberances 17 and situated on the apposed surfaces 35, 45 parallel to a straight line situated in the central plane 19 (FIG. 1). For an easier introduction of the intervertebral implant 1 into the intervertebral space, the height of the rib 38 decreases towards the dorsal lateral surface 32.

Figure 13:
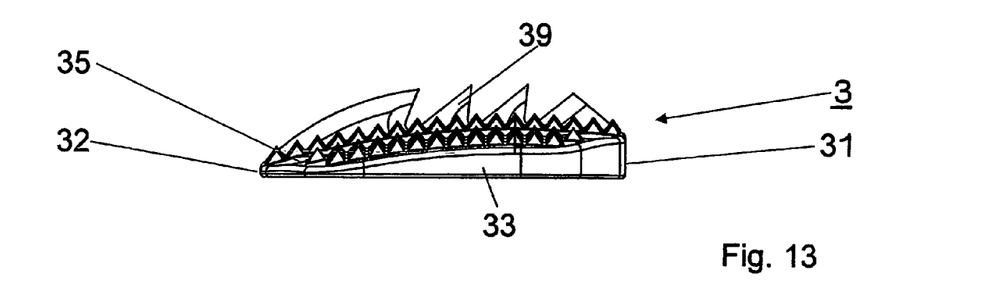
FIG. 13 is a lateral view of the top part of a further embodiment of the intervertebral implant with locking means.
Figure 14:
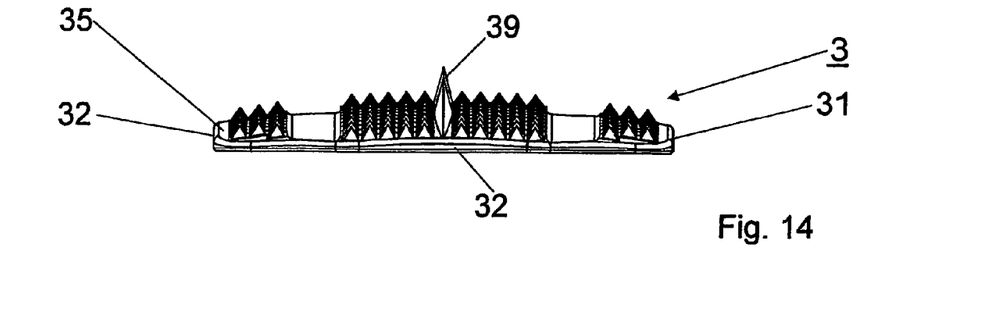
FIG. 14 is a dorsal view of the top part of the embodiment of the intervertebral implant illustrated in FIG. 7 with locking means.

A further embodiment of the protuberances 18 is illustrated in FIGS. 13 and 14. Serrations 39, which are taller than the pyramid-shaped protuberances 17, are constructed partly with saw-tooth shapes, wherein the steeper flank is facing the ventral lateral surface 31. In this case the serrations 39 are situated on a straight line situated in the central plane 19 (FIG. 1) and extend from the ventral lateral surface 31 up to the dorsal lateral surface 32.

In FIGS. 11-14 only the top part 3 is illustrated in the form of an example. In an analogous manner the same construction of the protuberances 18 with pyramid-shaped protuberances 17, a rib 38 (FIGS. 11 and 12) or serrations 39 (FIGS. 13 and 14) can be applied to the bottom part 4.

By virtue of these developments of the protuberances 18, serrations 39 or rib 38, the torque about an axis of rotation, intersecting the apposed surfaces, can be better transferred from the bodies of the vertebra to the intervertebral implant 1, and further the surface area to which the bones can adhere is increased. An advantage of the serrations 39 is, that they can more easily penetrate into the end plates of the adjacent bodies of the vertebra.

In another embodiment at least one of the protuberances 18, serrations 39 or rib 38 are coated with a material that can be integrated with bone or even replaced by new bone grown by the body. Exemplary materials include hydroxylapatite or a bi-phased hydroxylapatite-tricalcium phosphate mixture.

In another embodiment the cross-section of the grooves 22, 23, situated transversely to the central plane 19, narrows towards the top and bottom surfaces of the two parts, so that the grooves 22, 23 are constructed, for example, as dovetail guides, and can absorb forces parallel to the central axis 2 in both directions.

In a further embodiment the convex joint part 12 comprises a spherical first articular surface 10 and the joint shell 13 a second articular surface 11 corresponding to and preferably matching the first articular surface. By virtue of the spherical construction of the articular surfaces 10, 11 the advantage that both parts can pivot polyaxially relative one another is achieved.

The dimensions of the articular surfaces 10,11 depend from the application, while in the various embodiments the radius of the first articular surface 10 of the convex joint part 12 is between about 3 mm and about 25 mm, preferably between about 4 mm and about 20 mm.

In yet another embodiment the convex joint part 12 and the joint shell 13 are made from a metal/plastics material pair. Such a pairing has the advantage of allowing a low frictional force between the convex joint part 12 and the joint shell 13. Further the pairing allows a damping of axial forces on the joint 9. Still further there are already proven pairings of replacement materials for joints that can be used. An exemplary pairing is a highly cross-linked polyethylene (X-UHM-WPE) and a cobalt/chromium alloy. However one of skill in the art will realize that a variety of other pairings is possible.

In another embodiment the articular surfaces 10,11 are coated to reduce the coefficient of friction between the two surfaces 10,11. Exemplary coatings include titanium carbide or amorphous carbon (ADLC). However, one of skill in the art will realize that a variety other coatings are possible.

In yet another embodiment the two parts are coated with titanium on the apposed surfaces.

In a further embodiment the apposed surfaces have a convex shape and are adapted to suit the natural cover and base surfaces, respectively, of the adjacent bodies of the vertebra.

In yet another embodiment the intervertebral implant comprises a sterile packaging, so that the pre-assembled intervertebral implant, fixed by the locking means 21, can be implanted by the surgeons in-situ without any prior manipulation.

In a method of inserting the intervertebral implant, a surgeon may present the intervertebral disk anteriorly by a transperitoneal or retroperitoneal access. He removes the intervertebral disk (diskectomy) up to the stage required for the width of the implant. By means of a suitable instrument the surgeon can distract the intervertebral space so as to produce a relief (decompression) with the subsequently inserted intervertebral implant 1. With the aid of a trial implant the surgeon can determine the optimal size of implant.

The surgeon may then insert the intervertebral implant 1 into the prepared intervertebral disk space by means of a suitable instrument and the temporary locking means 21. The final position of the implant may be found by striking and shifting the intervertebral implant 1, using suitable instruments. So that the implant allow functional mobility, the temporary locking means and the associated instruments are removed. Finally, the surgeon can extract the distractor and close the wound.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed:

1. An intervertebral implant comprising:
a top part having a top surface, a dorsal side surface, a ventral side surface, a first top lateral side surface, a second top lateral side surface, and a bottom surface opposite the top surface, wherein the top surface is suitable for contacting the vertebra adjacent and above the site of implantation and the bottom surface includes a first top curved groove and a second top curved groove extending from the ventral side for engaging first and second jaws associated with an insertion instrument, the first top groove and the second top groove, respectively, lie substantially below the top surface of the top part; and
a bottom part having a bottom surface, a dorsal side surface, a ventral side surface, a first bottom lateral side surface, a second bottom lateral side surface, and a top surface opposite the bottom surface, wherein the bottom surface is suitable for contacting the vertebra adjacent and below the site of implantation, and the top surface includes a first bottom curved groove and a second bottom curved groove extending from the ventral side for engaging the first and the second jaws associated with the insertion instrument, the first bottom groove and the second bottom groove, respectively, lie substantially above the bottom surface of the bottom part;
a central plane between the first top lateral side surface and the second top lateral side surface and between the first bottom lateral side surface and the second bottom lateral side surface, the central plane substantially bisecting the top part and substantially bisecting the bottom part;
a central axis lying in the central plane intersecting the top part and the bottom part; and
a joint arranged between the top part and the bottom part, comprising a convex joint part having a first articular surface and a joint shell having a second articular surface corresponding to the joint shell and mounted in a sliding manner on the first articular surface.

2. The implant of claim 1, wherein the insertion instrument has a pliers-like construction and includes the first and the second jaws which can move relative to one another about a pivot hinge and which can be introduced into the grooves.

3. The implant of claim 2, wherein the axis of rotation of the pivot hinge extends parallel to the central axis.

4. The implant of claim 1, wherein the top surface of the top part and the bottom surface of the bottom part have a substantially convex construction.

5. The implant of claim 1, wherein the top surface of the top part and the bottom surface of the bottom part are provided at least partially with macroscopic pyramid-shaped protuberances.

6. The implant of claim 5, wherein the pyramid-shaped protuberance each have a volume between about 0.12 mm$^3$ and about 1.4 mm$^3$.

7. An intervertebral implant comprising:
a top part having a top surface, a dorsal side surface, a ventral side surface, a first top lateral side surface, a second top lateral side surface, and a bottom surface opposite the top surface, wherein the top surface is suitable for contacting the vertebra adjacent and above the site of implantation and the bottom surface includes a first top curved groove and a second top curved groove extending from the ventral side for engaging first and second jaws associated with an insertion instrument; and a bottom part having a bottom surface, a dorsal side surface, a ventral side surface, a first bottom lateral side surface, a second bottom lateral side surface, and a top surface opposite the bottom surface, wherein the bottom surface is suitable for contacting the vertebra adjacent and below the site of implantation, and the top surface includes a first bottom curved groove and a second bottom curved groove extending from the ventral side for engaging the first and the second jaws associated with the insertion instrument;

a central plane between the first top lateral side surface and the second top lateral side surface and between the first bottom lateral side surface and the second bottom lateral side surface, the central plane substantially bisecting the top part and substantially bisecting the bottom part;

a central axis lying in the central plane intersecting the top part and the bottom part; and a joint arranged between the top part and the bottom part, comprising a convex joint part having a first articular surface and a joint shell having a second articular surface corresponding to the joint shell and mounted in a sliding manner on the first articular surface;

wherein the first and second top curved grooves are curved towards the central axis; and the first and second bottom curved groove are curved towards the central axis.

8. An intervertebral implant comprising:

a top part having a top surface, a dorsal side surface, a ventral side surface, a first top lateral side surface, a second top lateral side surface, and a bottom surface opposite the top surface, wherein the top surface is suitable for contacting the vertebra adjacent and above the site of implantation and the bottom surface includes a first top curved groove and a second top curved groove extending from the ventral side for engaging first and second jaws associated with an insertion instrument; and a bottom part having a bottom surface, a dorsal side surface, a ventral side surface, a first bottom lateral side surface, a second bottom lateral side surface, and a top surface opposite the bottom surface, wherein the bottom surface is suitable for contacting the vertebra adjacent and below the site of implantation, and the top surface includes a first bottom curved groove and a second bottom curved groove extending from the ventral side for engaging the first and the second jaws associated with the insertion instrument;

a central plane between the first top lateral side surface and the second top lateral side surface and between the first bottom lateral side surface and the second bottom lateral side surface, the central plane substantially bisecting the top part and substantially bisecting the bottom part;

a central axis lying in the central plane intersecting the top part and the bottom part; and a joint arranged between the top part and the bottom part, comprising a convex joint part having a first articular surface and a joint shell having a second articular surface corresponding to the joint shell and mounted in a sliding manner on the first articular surface;

wherein: the first and second top curved grooves are designed so that the distance between the first top curved groove and the second top curved groove decreases as a distance of the grooves from the ventral side increases; and the first and second bottom curved grooves are designed so that the distance between the first bottom curved groove and the second bottom curved groove decreases as a distance of the grooves from the ventral side increases.

9. An intervertebral implant comprising:

a top part having a top surface, a dorsal side surface, a ventral side surface, a first top lateral side surface, a second top lateral side surface, and a bottom surface opposite the top surface, wherein the top surface is suitable for contacting the vertebra adjacent and above the site of implantation and the bottom surface includes a first top curved groove and a second top curved groove extending from the ventral side for engaging first and second jaws associated with an insertion instrument; and a bottom part having a bottom surface, a dorsal side surface, a ventral side surface, a first bottom lateral side surface, a second bottom lateral side surface, and a top surface opposite the bottom surface, wherein the bottom surface is suitable for contacting the vertebra adjacent and below the site of implantation, and the top surface includes a first bottom curved groove and a second bottom curved groove extending from the ventral side for engaging the first and the second jaws associated with the insertion instrument;

a central plane between the first top lateral side surface and the second top lateral side surface and between the first bottom lateral side surface and the second bottom lateral side surface, the central plane substantially bisecting the top part and substantially bisecting the bottom part;

a central axis lying in the central plane intersecting the top part and the bottom part; and a joint arranged between the top part and the bottom part, comprising a convex joint part having a first articular surface and a joint shell having a second articular surface corresponding to the joint shell and mounted in a sliding manner on the first articular surface;

wherein: a size of each of the first top curved groove and the second top curved groove decreases as a distance from the ventral side increases; and a size of each of the first bottom curved groove and the second bottom curved groove decreases as a distance from the ventral side increases.

* * * * *